United States Patent [19]

Petrik et al.

[11] Patent Number: 4,460,605

[45] Date of Patent: Jul. 17, 1984

[54] 2-[2'-HYDROXY-3'-(1,1-DIMETHYL-PROPYLAMINO)-PROPOXY]-β-PHENYL-PROPIOPHENONE, ITS PHYSIOLOGICALLY ACCEPTABLE ACID ADDITION SALTS, AND PHARMACEUTICAL COMPOSITIONS

[75] Inventors: Gerd Petrik; Rolf Sachse, both of Berlin, Fed. Rep. of Germany

[73] Assignee: Helopharm W. Petrik & Co., Berlin, Fed. Rep. of Germany

[21] Appl. No.: 410,933

[22] Filed: Aug. 24, 1982

[30]     Foreign Application Priority Data

Aug. 26, 1981 [DE]  Fed. Rep. of Germany ....... 3133814

[51] Int. Cl.³ .................. A61K 31/135; C07C 97/10
[52] U.S. Cl. ..................................... 424/330; 564/349
[58] Field of Search .................... 564/349; 424/330

[56]              References Cited
           FOREIGN PATENT DOCUMENTS 2001431  7/1971  Fed. Rep. of Germany ...... 564/349

OTHER PUBLICATIONS

*Arzneimittel Forschung,* (Drug Research), vol. 26, No. 10, (1976), pp. 1849–1857, Hapke et al.

*Primary Examiner*—Natalie Trousof
*Assistant Examiner*—Patricia M. Scott

[57]            ABSTRACT

The 2-[2'-hydroxy-3'-(1,1-dimethylpropylamino)-propoxy]-β-phenylpropiophenone of formula I

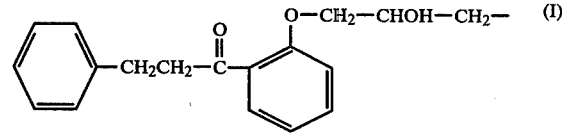

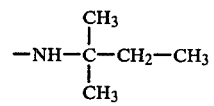

and its acid addition salts are described. Moreover, the preparation of this compound and of its acid addition salts is described. The compound and its acid addition salts have an antiarrhthymic effect. They can therefore be used for treating heart rhythm disorders.

4 Claims, No Drawings

2-[2'-HYDROXY-3'-(1,1-DIMETHYL-PROPYLAMINO)-PROPOXY]-β-PHENYLPROPIOPHENONE, ITS PHYSIOLOGICALLY ACCEPTABLE ACID ADDITION SALTS, AND PHARMACEUTICAL COMPOSITIONS

BACKGROUND OF THE INVENTION

The invention relates to the novel 2-[2'-hydroxy-3'-(1,1-dimethylpropylamino)-propoxy]-β-phenylpropiophenone of formula I

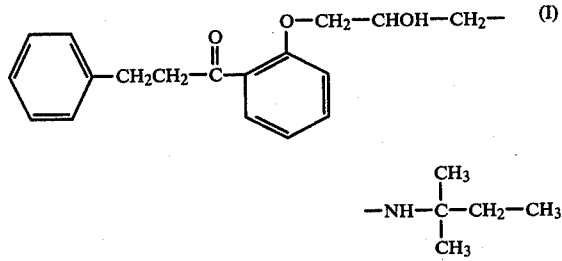

and its physiologically acceptable acid addition salts. The invention also relates to pharmaceutical compositions containing the compound of formula I or its physiologically acceptable acid addition salt. The compound is also called hereinafter diprafenone.

German Pat. No. 2 001 431 discloses 2-(2'-hydroxy-3'-alkylaminopropoxy)-β-phenylpropionphenones of the general formula

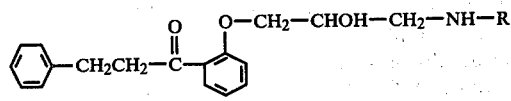

and its acid addition salts. The residue R of this formula means the n-propyl group (—CH$_2$—CH$_2$—CH$_3$), the n-butyl group (—CH$_2$—CH$_2$—CH$_2$—CH$_3$), the 1-methyl propyl group (—CH(CH$_3$)—CH$_2$—CH$_3$) or the tert-butyl group (—C(CH$_3$)$_3$).

This patent also describes a process for preparing these compounds. Said known compounds and their salts constitute pharmaceuticals. Investigations on isolated guinea pig hearts (method according to Langendorff) have shown that these compounds produce a significant increase in the coronary flow. Moreover, the n-propylamino compound (R=n-C$_3$H$_7$, hereinbelow called propafenone) is the only one of the compounds described which in addition shows an antiarrhythmic effect. In experiments with animals (dogs, cats and rabbits) showing model arrhythmias the antiarrhythmic effect of propafenone appeared after intravenous (1 mg/kg) and oral (2–10 mg/kg) administration; see H. J. Hapke and E. Prigge, Arzneim. Forsch. (Drug Res.) 26,10, 1849–1857 (1976).

The model arrhythmias were induced by the following measures: infusion of adrenalin plus chloroform inhalation or by infusion of digoxin, calcium chloride or aconitine or by occlusion of the left coronary artery. In average (1–3 mg/kg) and higher (5 mg/kg) intravenous doses propafenone has a hypotensive, negative inotropic effect and dilates the coronary arteries. With doses producing an antiarrhythmic effect, the heart rate is not substantially affected.

At present propafenone is used in human medicine as antiarrhythmic with local anaesthetic, quinidine-like and also β-receptor blocking effect for the therapy of heart rate disorders; see for instance W. Baedeker, G. Klein and G. Ertl, Herz-Kreislauf, Zeitschrift für Kardiologie and Angiologie, vol. 11, 330 (1979).

Investigations with the other three 2-(2'-hydroxy-3'-alkylaminopropoxy)-β-phenylpropiophenone compounds known from German Pat. No. 2 001 431, i.e. the n-butylamino, 1-methylpropylamino and the tert-butylamino compounds have shown that these compounds produce practically no antiarrhythmic effect when administered in average (1–3 mg/kg) intravenous doses in tests with animals having model arrhythmias.

SUMMARY OF THE INVENTION

It is the object of the invention to provide a novel 2-(2'-hydroxy-3'-alkylaminopropoxy)-β-phenylpropiophenone and its acid addition salts which is distinguished by a substantially higher antiarrhythmic but no substantially higher toxic effect than the propafenone. It is another object of the invention to provide a process for producing this compound and its acid addition salts. Finally, it is an object of the invention to provide pharmaceutical compositions for treating heart rhythm disorders which contain this compound or its acid addition salt, preferably a physiologically acceptable acid addition salt.

The invention thus relates to the 2-[2'-hydroxy-3'-(1,1-dimethylpropylamino)-propoxy]-β-phenylpropiophenone (diprafenone) of the above-mentioned formula I or its physiologically acceptable acid addition salts.

The invention also relates to a pharmaceutical composition containing diprafenone of formula I or its salts in combination with a pharmaceutical carrier, and to a method for treating heart rhythm disorders in a patient requiring such treatment by administering an effective amount of diprafenone or its salts.

DETAILED DESCRIPTION OF THE INVENTION

The compound of formula I can be prepared according to the following process:

Reaction of a phenol ether of the general formula II

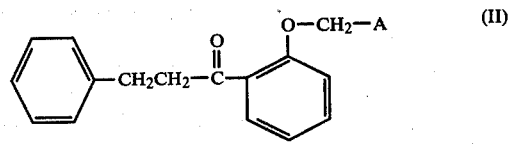

wherein A represents the residue

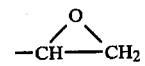

or —CHOH—CH$_2$—B and B is a leaving group, with the 1,1-dimethylpropylamine of the formula III

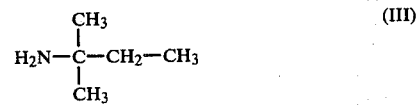

The 1,1-dimethylpropylamino compound obtained is optionally converted with an acid into an acid addition salt. The reaction can for instance be performed according to the method described in German Pat. No. 2 001 431 and German Offenlegungsschrift No. 2 007 751.

Preferably, the leaving group B is a halogen atom, in particular a chlorine, bromine or iodine atom. Aromatic or aliphatic sulfonic acid groups are also useful, such as the p-toluene sulfonic acid group, the p-bromobenzene sulfonic acid group or the methane sulfonic acid group.

The reaction is carried out at temperatures ranging from 10° to 120° C., that is at room temperature or at higher temperatures, preferably at temperatures ranging from 50° to 120° C., at atmospheric pressure or in a closed vessel at elevated pressure.

The starting compounds of formulae II and III can be reacted without diluents or solvents, However, the reaction is preferably carried out in the presence of an inert diluent or solvent, such as a lower alcohol having 1 to 4 carbon atoms, as for instance methanol, ethanol or propanol, preferably isopropanol or ethanol, a lower saturated dialkylether, dialkylglycolether or cyclic ether, such as diethylether, 1,2-dimethoxyethane, tetrahydrofuran or dioxane, a benzene hydrocarbon, such as benzene itself or an alkyl benzene, in particular toluene or xylene, or an aliphatic hydrocarbon, such as hexane, heptane or octane, dimethylsulfoxide or in the presence of water or mixtures of the mentioned solvents.

When used in excess, the 1,1-dimethylpropylamine (2-methyl-2-aminobutane) may also be a suitable diluent or solvent.

Lower alcohols, in particular ethanol or isopropanol are preferred solvents in reacting the compound having formula II, in which A represents the residue

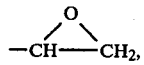

with the amine of formula III, the reaction being preferably carried out at temperatures ranging from 50° to 120° C. The reaction can optionally be performed in a closed vessel under pressure.

In nucleophilic substitution of a residue B, as solvent, a cyclic aliphatic ether, especially tetrahydrofuran or dioxane or dimethyl sulfoxide and temperatures ranging from 90° to 120° C. are preferred. The reaction can optionally be carried out in the presence of a catalytic amount of sodium or potassium iodide.

The phenol ether of general formula II can optionally also be used in the form of a mixture of an epoxide with a halohydrin, since in the technical preparation of the starting compounds such mixtures can possibly be formed.

In a useful embodiment for the nucleophilic substitution of the residue B by the amine of the formula III, the reaction is carried out in the presence of a base as acid-binding agent. Preferred bases are alkali metal hydroxides, alkali metal carbonates, alkali metal bicarbonates, alkali metal alcoholates, and in particular methylates and ethylates, or a tertiary amine, such as pyridine or a trialkylamine, such as trimethylamine or triethylamine. Of the alkali compounds, those of sodium and potassium are especially useful. The base is used in stoichiometrical or slightly excess amounts.

When used in excess amounts the amine used for the reaction may at the same time serve as acid-binding agent.

The completeness of the reaction depends on the reaction temperature and is in general achieved within 2 to 15 hours. The reaction product can be obtained in a conventional manner, for instance by filtration or distillation of the diluent from the reaction mixture. The compound obtained is purified in the usual manner, for instance by recrystallization from a solvent, conversion into an acid addition salt or by column chromatography.

The phenol ether of general formula II can be obtained by alkylating 2-hydroxy-β-phenylpropiophenone having the formula IV

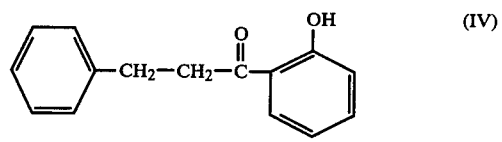

with an epihalohydrin or an α,ω-dihalo-2-propanol. Examples of epihalohydrins are epichlorohydrin, epibromohydrin and epiiodo hydrin. Examples of α,ω-dihalo-2-propanols are especially 1,3-dichloro-2-propanol and 1,3-dibromo-2-propanol.

The reaction of the compound IV for preparing the starting compounds of formula II is expediently carried out at temperatures ranging from 0° to 120° C. and normal pressure or in a closed vessel at elevated pressure. Suitable solvents or diluents are a lower aliphatic ketone, such as acetone, methylethyl ketone or methylisobutylketone, a lower alcohol having 1 to 4 carbon atoms, such as methanol, ethanol, propanol or butanol, a lower aliphatic or cyclic ether, such as diethylether, tetrahydrofuran or dioxane, a dialkylformamide, such as dimethylformamide or diethylformamide, or dimethylsulfoxide or hexamethylphosphoric acid triamide or an excess amount of the alkylating agent.

The reactions are preferably carried out in the presence of a base as acid-binding agent. Suitable bases are alkali metal carbonates, alkali metal bicarbonates, alkali metal hydroxides, alkali metal hydrides or alkali metal alcoholates, in particular those of sodium and potassium, basic oxides, such as aluminum oxide or calcium oxide, organic tertiary bases, such as pyridine, lower trialkyl amines, such as trimethyl amine or triethyl amine, or piperidine. The bases can be used in catalytic or stoichiometric amounts or in slightly excess amounts with respect to the alkylating agent used.

2-Hydroxy-β-phenylpropiophenone is preferably reacted with epichlorohydrin, epibromohydrin or 1,3-dibromopropanol-2 in a polar, aprotic solvent, in particular dimethylsulfoxide, at temperatures ranging from 0° to 50° C. in the presence of at least one mole equivalent base, in particular sodium hydride, based on the alkylating agent.

The starting compound of formula IV, that is the 2-hydroxy-β-phenylpropiophenone, and its preparation are known.

The compound of formula I exhibits a chirality center on the carbon atom in the 2-position of the aliphatic side chain. In general it is obtained as racemate which can be resolved into the optically active antipodes by known methods, for instance by the formation of diastereomeric salts with optically active acids, such as dibenzoyl tartaric acid, camphor-10-sulfonic acid, ditoluyl tartaric acid or 3-bromo-camphor-8-sulfonic acid.

The compound of formula I obtained according to the invention is optionally converted into an acid addition salt, preferably into a salt of a physiologically acceptable acid. Usual physiologically acceptable inorganic and organic acids are for instance hydrochloric acid, hydrobromic acid, phosphoric acid, sulfuric acid, oxalic acid, maleic acid, fumaric acid, lactic acid, tartaric acid, malic acid, citric acid, salicyclic acid, adipic acid and benzoic acid. Other suitable acids are described for instance in Fortschritte der Arzneimittelforschung, vol. 10, pages 224–225, Birkhäuser publishers, Basle and Stuttgart, 1966, and Journal of Pharmaceutical Sciences, vol. 66, pages 1–5 (1977). Hydrochloric acid is preferred.

The acid addition salts are normally obtained in a conventional manner by mixing the free base or its solutions with the corresponding acid or its solutions in an organic solvent, for instance a lower alcohol, such as methanol, ethanol, n-propanol or isopropanol, or a lower ketone, such as acetone, methylethyl ketone or methyl-isobutyl ketone, or an ether, such as diethyl ether, tetrahydrofuran or dioxane. Mixtures of the mentioned solvents can also be used for better crystal deposition. Moreover pharmaceutically acceptable aqueous solutions of acid addition salts of the compound of formula I can be prepared in an aqueous acid solution.

The acid addition salts of the compound of formula I can be converted into the free base in a manner known per se, as for instance with alkalis or ion exchangers. Further salts can be obtained from the free base by reaction with inorganic or organic acids, in particular with those which are suitable for the formation of therapeutically useful salts. These and other salts of the new compound, such as the picrate can also lend themselves to the purification of the free base wherein the free base is converted into a salt, which is separated and the base is again liberated from the salt.

The present invention also relates to pharmaceutical compositions for oral, rectal, intravenous or intramuscular application, which apart from the usual carriers and diluents contain the compound of formula I or its acid addition salt as active ingredient. Furthermore it relates to the use of the new compound and its physiologically acceptable salts in the treatment of heart rhythm disorders.

The pharmaceutical compositions of the invention are prepared in a conventional manner with the usual solid or liquid carriers or diluents and the conventional pharmaceutical adjuvants in a suitable dosage in accordance with the desired form of application. The preferred preparations are compositions in dosage unit form for oral application. Such pharmaceutical forms are for instance tablets, filmcoated tablets, dragees, capsules, pills, powders, solutions or suspensions or depot preparations.

Parenteral preparations, such as injection solutions, are of course also suitable. Another pharmaceutical form to be mentioned is, for instance, the suppositories.

Corresponding tablets can be obtained for instance by mixing the active ingredient with known auxiliaries, for instance with inert diluents, such as dextrose, sugar, sorbitol, mannitol, polyvinylpyrrolidone, disintegrating agents, such as corn starch or alginic acid, binders, such as starch or gelatine, lubricants, such as magnesium stearate or talcum and/or agents for achieving a depot effect, such as carboxypolymethylene, carboxymethylcellulose, cellulose acetatephthalate or polyvinylacetate. The tablets may comprise several layers.

Dragees can be prepared correspondingly by coating cores which have been manufactured analogously to the tablets with compositions commonly used in dragee coatings, such as polyvinylpyrrolidone or shellac, gum arabic, talcum, titanium dioxide or sugar. The dragee shell may also consist of several layers, wherein the auxiliaries mentioned above in connection with the tablets may be used.

Solutions or suspensions comprising the inventive active ingredient may additionally contain flavoring agents, such as saccharin, cyclamate or sugar and for instance aromatics, such as vanillin or orange extract. Moreover, they may contain suspension auxiliaries, such as sodium carboxymethyl cellulose or preservatives, such as p-hydroxybenzoates. Capsules containing the active ingredient can for instance be prepared by mixing the active ingredient with an inert carrier, such as lactose or sorbitol, and encapsulating it in gelatine capsules.

Suitable suppositories can be prepared by mixing the active ingredient with corresponding carriers, such as neutral fats or polyethylene glycol or their derivatives.

In humans, the single dose is
from 0.5–5 mg/kg for oral application
from 0.05–2 mg/kg for intravenous application
from 0.1–3 mg/kg for intramuscular application
from 0.5–10 mg/kg for rectal application.

The administration of diprafenone will ultimately be determined by the judgement of the attaching physician and the particular condition of the patient being treated. The routes and dosage amounts are those generally suggested for use.

Under the above-mentioned conditions described by H. J. Hapke and E. Prigge, Arzneim.-Forsch. (Drug Res.), loc. cit. in model arrhythmias, the compound of formula I, i.e. the 2-[2'-hydroxy-3'-(1,1-dimethylpropylamino)-propoxy]-$\beta$-phenylpropiophenone (diprafenone) surprisingly already shows an antiarrhythmic effect at 0.05 mg/kg in intravenous application, that is with the twentieth part of the necessary dose of the reference substance propafenone.

This surprisingly high antiarrhythmic effect is not accompanied by a correspondingly great increase of toxicity. This can be seen from a comparison of the $LD_{50}$ values in rat and dog which are summarized in table I.

TABLE I

| $LD_{50}$ (mg/kg) | propafenone-HCl | diprafenone-HCl |
| --- | --- | --- |
| rat i.v. | 18.8 | 16.9 |
| rat oral | 760 | 1080 |
| dog i.v. | 15.0 | 10.0 |

From this it can be seen that the therapeutic quotient of diprafenon is increased from 10 to 20 times as compared to propafenone.

The antiarrhythmic effect of the compound of formula I was tested in dogs according to the method of Hapke and Prigge, Arzneim.-Forsch. (Drug Res.), loc. cit. A model arrhythmia which was essentially characterized by ventricular extrasystoles at absolute arrhythmia was produced by infusion of chloroform and adrenalin (epinephrine). At the onset of these rhythm disorders the inventive compound was injected intravenously as aqueous solution of the hydrochloride.

An intravenous dose as small as 0.05 mg/kg was fully effective within 45 seconds in all dogs treated with it, that is the sinus rhythm is the electrocardiogram (ECG) became normal.

Again in dogs, the excellent antiarrhythmic effect could be observed after oral administration too. Rhythm disorders were produced by occlusion of a branch of the coronary vessels. The inventive compound was administered intragastrically in the form of the hydrochloride the next day. Extrasystoles were observed unchanged for 10 minutes after application of 10 mg/kg. 30 minutes after application no extrasystoles could be observed. The ECG remained normal for the 24 hours during which it was observed.

Table II shows further results of pharmacological tests on dogs with the inventive compound in the hydrochloride form and with propafenone-HCl. For the test method see H. J. Hapke and E. Prigge, Arzneim.-Forsch. (Drug Res.), loc. cit.

All listed test results suggest that the compound of formula I (diprafenone) can be expected to be also useful in human medicine as antiarrhythmic like propafenone, however in substantially lower doses and thus with lower toxicity.

TABLE II

| Circulation parameters other test criteria | Test comp. | Dosage (mg/kg body weight) i.v. | | | | | | | | |
|---|---|---|---|---|---|---|---|---|---|---|
| | | 0.05 | 0.1 | 0.2 | 0.3 | 0.5 | 1.0 | 3.0 | 5.0 | 10.0 |
| Systolic blood pressure | D | | 0 | 0 | | −13 | −17 | −45 | | |
| (A. femoralis), mm Hg | P | | | | 0 | | 0 | −30 | | −65 |
| Diastolic blood pressure | D | | 0 | 0 | | −16 | −24 | −39 | | |
| (A. femoralis), mm Hg | P | | | | 0 | | 0 | −40 | | −60 |
| Heart beat rate | D | | 0 | 0 | | −8 | −22 | −24 | | |
| change min$^{-1}$ | P | | | | 0 | | 0 | 0 | | |
| Left ventricular | D | | 0 | 0 | | 0 | 0 | −46 | | |
| peak pressure, mm Hg | P | | | | 0 | | −5 | −25 | −42 | −70 |
| Maximum rate of pressure | D | | 0 | 0 | | 0 | 0 | −30 | | |
| rise (dp/dt) % | P | | | | 0 | | 0 | −29 | −47 | −62 |
| Peripheral blood flow | D | | 0 | 0 | | 0 | 0 | 0 | | |
| volume, % (A. femoralis) | P | | | | 0 | | +10 | +36 | | |
| Coronary flow volume % | D | 0 | | | 0 | | 0 | +56 | | |
| | P | | | | | | +14 | +30 | +43 | +67 |
| Antiarrhythmic effect | D | + | + | + | | + | + | | | |
| (CHCl$_3$—adrenalin-model arrhythmia) | P | 0 | 0 | 0 | 0 | 0 | + | + | | |

D = Diprafenone, P = propafenone, 0 = not significantly different from the starting value; + = significant effect.

It is surprising and could not be expected that when used in comparable doses, the inventive compound does not have an effect on the peripheral and coronary circulation, despite its striking similarity with the known 2-(2'-hydroxy-3'-alkylaminopropoxy)-β-phenylpropiophenone compounds and shows an approximately 20 times greater effect in heart rhythm disorders than propafenone in spite of having approximately the same hemodynamic activity. The compound of formula I can therefore be used in substantially lower doses than propafenone. As a result, the side effects in the treatment of heart rhythm disorders are considerably reduced.

Moreover it is remarkable that contrary to propafenone, the compound of the invention already produces a reduction of the heart beat rate at doses of 0.5 mg/kg i.v., which is desirable in tachycardic heart rhythm disorders.

The invention is illustrated by the examples.

EXAMPLE 1

(a) Preparation of 2-(2',3'-epoxypropoxy)-β-phenyl-propiophenone 22.6 g (0.1 mole) of 2-hydroxy-β-phenylpropiophenone are dissolved with 150 ml of 1-chloro-2,3-epoxypropane. After addition of 12 g of potassium carbonate the reaction mixture is heated under agitation and refluxing until the reaction is demonstrated by high pressure liquid chromatography to be completed. The reaction mixture is then allowed to cool. The potassium chloride formed is subsequently filtered off. The filtrate is condensed at reduced pressure, while excess 1-chloro-2,3-epoxypropane is thereby distilled from the resultant 2-(2',3'-epoxypropoxy)-β-phenylpropiophenone. The crude product obtained is a yellowish oil which solidifies at room temperature when allowed to stand for some time (yield 28 g; 98%). The product does not need to be purified for the next stage. The pure substance obtained by recrystallization from the fourfold amount of methanol has a melting point of 56° C.

| $C_{18}H_{18}O_3$; | C | H |
|---|---|---|
| calculated | 76.58 | 6.42 |
| found | 76.92 | 6.38 |

(b) Preparation of 2-[2'-hydroxy-3'-(1,1-dimethyl-propylamino)-propoxy]-β-phenylpropiophenone-hydrochloride (diprafenone-HCl)

28 g (0.1 mole) of the compound obtained according to example 1a) are dissolved in 100 ml of methanol and treated with 26 g of 1,1-dimethylpropylamine (2-methyl-2-aminobutane). The mixture is then heated under refluxing for 4 hours while being stirred. The reaction mixture is then evaporated under reduced pressure. The resultant residue is dissolved in 100 ml of isopropanol while being heated and is adjusted to pH 1 with concentrated 36% hydrochloric acid. The mixture is allowed to stand at room temperature, while the hydrochloride precipitates in the form of crystals. The crude product obtained (about 36 g) is recrystallized from the same volume amount of isopropanol. The hydrochloride is obtained in a yield of approximately 33.0 g (81.3% in theory) in the form of a white crystalline substance having a melting point of 130° to 131° C. The analysis values of the pure substance correspond to the theoretical values.

| $C_{23}H_{32}NO_3Cl$ | C | H | N |
|---|---|---|---|
| calculated | 68.05 | 7.94 | 3.45 |
| found | 67.97 | 7.91 | 3.72 |

EXAMPLE 2

2-(2'-Hydroxy-3'-bromopropoxy)-β-phenylpropiophenone is reacted with an equivalent amount of 2-methyl-2-aminobutane in the presence of dimethylformamide as solvent and sodium carbonate as acid acceptor by refluxing for several hours. The diprafenone-hydrochloride with a melting point of 130° C. is obtained after the reaction mixture is worked up according to example 1b).

EXAMPLE 3

Example 2 is repeated with 2-(2'-hydroxy-3'-chloropropoxy)-β-phenylpropiophenone, obtaining the diprafenone-hydrochloride with a melting point of 130°–131° C.

EXAMPLE 4

Manufacturing process for Tablets

| | |
|---|---|
| diprafenone-HCl | 75.00 g |
| microcrystalline cellulose (powder, 50 μm) | 15.75 g |
| poly-(1-vinyl-2-pyrrolidone) | 5.00 g |
| hydroxypropylmethyl cellulose 2910 | 3.75 g |
| magnesium stearate | 0.50 g |
| | 100.00 g |

(b) Mixing and Granulating

The diprafenone-HCl is optionally screened. All materials except for magnesium stearate are then mixed in a mixer where they are moistened with a suitable amount of granulation liquid (for instance water or isopropanoldichloromethane 1:1). The moist mixture is passed through a suitable sieve, dried in a drying cabinet and screened again. The dried granulate is mixed with the magnesium stearate in the mixer.

(c) Precoating Composition

| | |
|---|---|
| talcum | 70.0% |
| calcium sulfate hemihydrate | 26.7% |
| finely dispersed silica | 3.3% |
| | 100.00% |

(d) Coating suspension for dragees

| | |
|---|---|
| saccharose | 47.8% |
| talcum | 9.6% |
| calcium sulfate hemihydrate | 4.8% |
| gum arabic | 3.6% |
| starch sirup | 3.2% |
| Macrogol 6000 | 2.9% |
| titanium (IV)-oxide | 1.6% |
| sodium dodecylsulfate | 0.1% |
| aqua dest. | 26.4% |
| | 100.00% |

Coating of Dragee Cores

The dragee cores are first moistened in a rotating vessel with dragee coating solution and then powdered with sufficient precoating composition for them to roll freely again. After the cores are dried, this process is repeated. The cores are then further dried in the drying cabinet. The cores are then layerwise coated with the dragee coating suspension until the desired final weight is achieved. The cores must be dried after application of each layer.

Pressing of Tablets

The mixture prepared according to (a) is pressed in a tablet press into tablets weighing from 40 to 400 mg. The pressing force and the tablet diameter are so selected that the disintegration time in the testing device according to the Eur. Pharm. is less than 15 minutes and the tablets are sufficiently stable mechanically.

EXAMPLE 5

Manufacturing Process for Film-coated Tablets

A. Ingredients (a) Tablet (see manufacturing process for tablets, example 4).

(b) Film Coating

The total amount applied is 5–20% of the tablet weight and consists of hydroxypropylmethyl cellulose 2910: 77%

Macrogol 6000 (plasticizer): 23%

B. Preparation of the Tablets (see manufacturing process for tablets, example 4)

C. Preparation of the Film-coated Tablets

The ingredients of the film-coating are dissolved in a suitable solvent (for instance water or ethanol/water 70:30). The tablets are sprayed in a film coating apparatus with the solution containing the film former and plasticizer and are dried in a hot air stream. The film-coated tablets are further dried in a drying cabinet.

EXAMPLE 6

Manufacturing Process for Dragees

A. Ingredients (a) Dragee core (see manufacturing process for tablets)

(b) Dragee shell the total amount applied is 25–100% of the core weight and consists of

| | |
|---|---|
| saccharose | 51.4% |
| talcum | 24.0% |
| calcium sulfate hemihydrate | 10.3% |
| starch sirup | 5.0% |
| gum arabic | 3.9% |
| Macrogol 6000 | 2.9% |
| titanium(IV)-oxide | 1.6% |
| finely dispersed silica | 0.8% |
| sodium dodecylsulfate | 0.1% |
| | 100.0% |

B. Preparation of the Dragee Cores (See manufacturing process for tablets)

C. Preparation of the Dragees

Composition of the dragee solution used,

Precoating composition and dragee suspension (a) dragee solution

| | |
|---|---|
| saccharose | 47.6% |
| starch sirup | 19.1% |
| gum arabic | 3.8% |
| aqua dest. | 29.5% |
| | 100.0% |

EXAMPLE 7

Manufacturing Process for Capsules

A. Dosage of the active ingredient of 75 mg and more

1. Ingredients

| | |
|---|---|
| diprafenone-HCl | 75.00 g |

| | |
|---|---|
| microcrystalline cellulose powder, 50 μm | 16.25 g |
| poly-(1-vinyl-2-pyrrolidone) | 5.00 g |
| hydroxypropylmethyl cellulose 2910 | 3.75 g |
| | 100.00 g |

2. Mixing and granulating according to example 4(b).

3. Filling the Granulate into Capsules

The granulate is filled by means of a capsulating machine into hard gelatine capsules of the size 3, 2, 1 or 0, the amount filled into each capsule depending on the desired dosage of the active ingredient.

B. Dosage of the active ingredient 30-75 mg

1. Ingredients

| | |
|---|---|
| diprafenone-HCl | 30.00-75.00 g |
| microcrystalline cellulose powder, 50 μm | 61.25-16.25 g |
| poly-(1-vinyl-2-pyrrolidone) | 5.00 g |
| hydroxypropylmethyl cellulose 2910 | 3.75 g |
| | 100.00 g |

The sum of the amounts of active ingredient and microcrystalline cellulose should always be 91.25 g. The amount of active ingredient is a thousand times the amount of the single dose.

2. Mixing and granulating according to example 4(b).

3. Filling the Granulate into Capsules 100 mg each of granulate are filled into hard gelatine capsules of size 3 or 2 with the aid of a capsulating machine.

EXAMPLE 8

Manufacturing Process for Ampoules

1. Ingredients diprafenone-HCl: 1.5 g water for injection purposes ad: 100.0 ml

2. Preparation of the Solution

90% of the water necessary for the batch selected are placed into the reaction vessel. The active ingredient is dissolved in said water under heat. The final volume is achieved by adding the necessary amount to the solution after cooling.

3. Filling the Solution into Ampoules

The finished solution is filled into glass ampoules, the amount filled in depending on the dosage desired. The glass ampoules are then sealed by fusion.

4. Sterilization

The ampoules are vapor-sterilized for 20 minutes at 120° C.

EXAMPLE 9

Manufacturing Process for Suppositories a.

diprafenone-HCl: 30-200 mg hard fat (melting point 35°-36.5° C.) ad: 2000 mg b. Preparation of the Melt Containing the Active Substance The amount of hard fat necessary for a specific number of suppositories is melted in a water bath at 40° C. The active ingredient is pressed through an 0.8 mm sieve and mixed into the melt to give a suspension.

c. Preparation of the Suppositories

The melt is allowed to cool down to 37°-38° C. and filled under steady stirring into suppository forms in such amounts that the weight of one suppository is 2000 mg. The suppository form is sealed after solidification of the melt.

What is claimed is:

1. 2-[2'-Hydroxy-3'-(1,1-dimethylpropylamino)-propoxy]-β-phenylpropiophenone of formula I

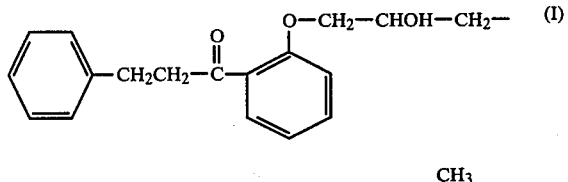

or its physiologically acceptable acid addition salts.

2. 2-[2'-Hydroxy-3'-(1,1-dimethylpropylamino)-propoxy]-β-phenylpropiophenone-hydrochloride according to claim 1.

3. A pharmaceutical composition suitable for treatment of heart rhythm disorders which comprises 2-(2'-hydroxy-3'-(1,1-dimethylpropylamino)-propoxy)-β-phenylpropiophenone or its physiologically acceptable acid addition salt in an amount sufficient to produce an antiarrhythmic activity and in combination with a pharmaceutical carrier.

4. A method of treating heart rhythm disorders which comprises administering to a patient requiring said treatment 2-[2'-hydroxy-3'-(1,1-dimethylpropylamino)-propoxy]-β-phenylpropiophenone or its physiologically acceptable acid addition salt in an amount sufficient to produce an antiarrhythmic activity.

* * * * *